United States Patent [19]

Rademacher

[11] Patent Number: 4,728,495

[45] Date of Patent: Mar. 1, 1988

[54] REMOVABLE DENTAL APPLIANCES

[75] Inventor: Leo Rademacher, Witten, Fed. Rep. of Germany

[73] Assignee: Thyssen Edelstahlwerke AG, Krefeld, Fed. Rep. of Germany

[21] Appl. No.: 841,606

[22] Filed: Mar. 20, 1986

[30] Foreign Application Priority Data

Mar. 22, 1985 [DE] Fed. Rep. of Germany ....... 3510331

[51] Int. Cl.$^4$ .............................................. C22C 30/00
[52] U.S. Cl. ..................... 420/583; 420/436; 420/437; 420/438; 420/439; 420/440; 433/207
[58] Field of Search ......................... 420/583, 435–440; 148/425, 442; 433/207

[56] References Cited

U.S. PATENT DOCUMENTS 3,865,585  2/1975  Rademacher ..................... 420/436

*Primary Examiner*—R. Dean
*Attorney, Agent, or Firm*—Cushman, Darby & Cushman

[57] ABSTRACT

The invention relates to removable dental appliances made of cobalt-chromium-cast alloys containing (in % by weight) 0,1 to 1,0% C, 0,05 to 0,5% N, 0,5 to 3,0% Si, 0,3 to 10,0% Mn, 20 to 35% Cr, 2 to 10% Mo, 5 to 40% Fe, at least 20% Cobalt as rest including incidental impurities.

7 Claims, No Drawings

REMOVABLE DENTAL APPLIANCES

BACKGROUND OF THE INVENTION

The invention relates to removable dental appliances consisting of cobalt-chromium cast alloys.

Non-iron metal cast alloys on cobalt-chromium base are in use for dental purposes for many years. As cobalt and chromium, they contain molybdenum as essential alloying constituents and, in some cases, also nickel. (F. R. Morral: Journal of Materials 1 (1966), pp. 384 to 412).

In the meantime, alloys on basis of about 62% Co, 30% Cr and 5% Mo were introduced for dental appliances. They have virtually completely substituted the originally used noble metal alloys. The Cr-Cr alloys have their outstanding properties, both from a clinical and from a technological point of view. A substantial advantage of the non-iron metal alloys over the noble metal alloys consists in their much lower price. Material costs have in the meantime come to the forefront of interest in the health service due to the curbing of costs ever more necessary for economical reason.

Apart from these purely economic aspects, the material properties which have to be maintained for the suitability of a metal alloy for the indication mentioned were not to be neglected.

To be regarded as a guideline for the requirements on the material properties are the recommendations of the International Organization for Standardization (ISO), because the non-iron metal cast alloys mentioned are marketed internationally. The standard concerned ISO 6871 "Dental base metal casting alloys" is at present being printed. The present draft for this ISO/DIS 6871 of 12.07.1984 includes the following recommendations already considered final and to be regarded as governing for the alloy to be used according to the invention:

1. The requirements on the chemical composition deal not only with alloys having a total content of chromium, cobalt and nickel of at least 85%, but alternatively also with alloys having a different composition, provided that they comply satisfactorily with the requirements on toxicity and corrosion resistance. As regards these requirements, it is further specified that the alloys give off neither constituents with harmful effect to the denture wearer, nor may they have visible signs of corrosion after having been subjected to an oral environment for one year. Furthermore, it is also recommended for beryllium-containing alloys that the Be content of 2% is not to be exceeded.
2. For the mechanical properties, the standard confines itself to a minimum yield strength of 500N/mm² and to a minimum elongation $A_5=3\%$ after fracture.
3. Finally, castability is to be ensured.

The price of the customary cobalt-chromium cast alloys is substantially determined by the content of cobalt. This is not only attributable to its by far predominant proportion but also to its high price in comparison with the remaining elements. Added to this is the fact that very considerable speculative, even if temporary, increases in the cobalt world market price have in recent years at times been a very great burden on the material costs of cobalt-chromium alloys. It is therefore object of the present invention to develop a non-iron metal cast alloy for dental purposes which is even more favourably in price than the customary cobalt-chromium alloys. At the same time however, it had to be borne in mind that the reduction in material costs aimed for was not to be bought by cost-increasing extra expenditure, for example in material production, in preparation of the prosthetic casting or in their subsequent finishing, and that no impairment of its properties in use occurred.

DESCRIPTION OF THE INVENTION

To achieve this object, according to the invention a cobalt-chromium base alloy is proposed containing (in % by weight):

0,1 to 1,0% carbon
0,05 to 0,5% nitrogen
0,5 to 3,0% silicon
0,3 to 10,0% manganese
20 to 35% chromium
2 to 10% molybdenum
5 to 40% iron
at least 20% cobalt as rest including incidental impurities.

A preferred composition consists of
0,1 to 0,5% carbon
0,05 to 0,5% nitrogen
0,9 to 2% silicon
1 bis 6% manganese
26 to 31% chromium
2 to 6% molybdenum
20 to 35% iron
rest cobalt.

The content of the sum of carbon and nitrogen of the alloy should preferably not exceed 1%.

As well as the substitution of cobalt by iron for the purposes of cost reduction, to adjust the material properties necessary at the same time with regard to production, processing and use, further-reaching technical alloying measures are taken. These consist primarily in a far-reaching variation of those elements which are also constituents of the known cobalt-chromium alloys. These variations have the effect of favourably influencing the melting and casting behaviour and the strength by the additions of nitrogen, aluminum, boron, columbium and/or titanium each up to 0,5%, preferably 0,01 to 0,2%. The strength may also be influenced by variation of the alloying elements contained in the basic composition. Higher amounts of the other alloying elements within the given ranges should be chosen if iron is added in the amount of 25 to 40%.

EXAMPLES

Table 1 contains the chemical composition of examples of the alloy according to the invention. In table 2, specifications on the corresponding mechanical properties and the corrosion behaviour of the alloys from table 1 are given.

In table 2, representative results for the known Co-Cr alloys (A) and for a noble metal alloy (B) having 76% noble metal content are also listed for comparison. For the examples of the alloy according to the invention, it is evident from the results that the yield strength decreases with increasing content of iron partly replacing cobalt. The requirement of the ISO Standard with respect to the yield strength of at least 500N/mm² is reached even at the highest iron content. The values for elongation of the examples according to the invention also lie considerably above the minimum value of 3% consistently required by the standards.

It is thereby ensured that the prosthetic casting may, if necessary, be readjusted and clasps cast at the same time can be activated without the risk of fracture.

The comparison of the alloys according to the invention with the known Co-Cr alloy A shows with regard to the mechanical properties (table 2) that half of them are equal or even superior.

The requirement of the ISO Standard on the chemical composition that the total content of cobalt and chromium is to be at least 85% is only met by examples 1, 2, 10 to 13, 17 and 18. Therefore, in accordance with the regulations of the ISO standard, corrosion tests in artificial salvia by the method of Fusayama et al. (see Journal of Dental Research, 42 (1963), page 1183) were conducted on fifteen alloys representative in their chemical composition. The values obtained thereby for the breakthrough potential which applies as a characteristic parameter for corrosion resistance can be taken from table 2. The breakthrough potential of the alloys according to the invention, with values between +790 and +1050 mV$_h$, lies clearly above the comparison value of +760 mV$_h$ of the known cobalt-chromium alloy A.

Surprisingly, the breakthrough potential of the alloys according to the invention increases with iron content. The maximum values reached of +1,000 to +1,050 mV$_h$ correspond to the comparison value of +1.000 mV$_h$ of the noble metal alloy B.

Additional corrosion investigations have also shown that the examples according to the invention are absolutely resistant to crevice corrosion and pitting, which could not have been expected.

On the basis of these results of corrosion testing, it is proven that the alloy according to the invention is corrosion-resistant under mouth conditions. To this extent, samples 3 to 9 and 14 to 16 also correspond to the requirements of the ISO Standard for chemical composition, although their total content of cobalt and chromium lies below 85%.

On the basis of the demonstrated corrosion resistance of the alloy according to the invention, in the claimed composition it may also be assumed that it can likewise be classified as harmless with regard to toxicity, so that it also meets the standard requirements in this respect.

To supplement the tests described for material properties on samples which are of significance for assessment of the properties in use, comprehensive suitability tests have also been conducted in a dental laboratory on the examples of table 1. On the basis of this, the alloy proposed according to the invention can be melted, cast and processed just as free from problems in every respect as the known Co-Cr alloys.

The test show that the proposed alloy represents a complete substitute for the known Co-Cr alloys and, owing to their lower price, can make a contribution to the curbing of costs in health service.

TABLE 1

| Melt No | Chemical analysis % by weight | | | | | | | | | |
|---|---|---|---|---|---|---|---|---|---|---|
| | C | Si | Mn | Cr | Fe | Mo | Al | B | N | other |
| 1 | 0,55 | 0,62 | 0,31 | 27,70 | 5,10 | 5,20 | 0,22 | — | 0,26 | — |
| 2 | 0,60 | 1,25 | 1,09 | 30,20 | 10,22 | 2,49 | 0,15 | — | 0,14 | — |
| 3 | 0,59 | 1,18 | 1,12 | 30,10 | 19,25 | 2,42 | 0,17 | — | 0,15 | — |
| 4 | 0,59 | 0,84 | 0,87 | 30,00 | 28,48 | 2,05 | 0,017 | — | 0,10 | — |
| 5 | 0,29 | 0,90 | 0,86 | 30,35 | 28,91 | 2,05 | 0,017 | — | 0,078 | — |
| 6 | 0,30 | 0,86 | 0,73 | 28,15 | 29,50 | 2,37 | n.b. | — | 0,21 | — |
| 7 | 0,28 | 1,01 | 0,81 | 28,35 | 29,00 | 5,16 | n.b. | — | 0,32 | — |
| 8 | 0,85 | 1,53 | 1,13 | 29,44 | 28,90 | 2,36 | 0,39 | — | 0,14 | — |
| 9 | 0,35 | 1,22 | 1,10 | 28,15 | 39,60 | 4,95 | 0,05 | 0,020 | 0,37 | — |
| 10 | 0,14 | 0,70 | 0,39 | 27,85 | 5,15 | 5,20 | 0,35 | n.b. | 0,27 | — |
| 11 | 0,13 | 0,64 | 0,35 | 27,42 | 5,07 | 5,07 | n.b. | 0,024 | 0,24 | 0,26 Nb |
| 12 | 0,13 | 0,71 | 0,35 | 27,84 | 5,12 | 5,01 | n.b. | 0,024 | 0,23 | 0,11 Ti |
| 13 | 0,12 | 0,95 | 2,76 | 27,79 | 2,35 | 5,14 | n.b. | 0,021 | 0,22 | — |
| 14 | 0,11 | 1,16 | 0,30 | 30,10 | 20,00 | 2,47 | 0,02 | — | 0,22 | — |
| 15 | 0,14 | 1,13 | 1,03 | 20,49 | 22,23 | 2,55 | 0,03 | — | 0,11 | — |
| 16 | 0,13 | 1,18 | 0,92 | 20,39 | 33,16 | 2,60 | 0,02 | — | 0,31 | — |
| 17 | 0,13 | 1,96 | 3,23 | 27,68 | 4,57 | 5,14 | — | — | 0,23 | — |
| 18 | 0,14 | 1,38 | 5,06 | 27,63 | 4,91 | 5,54 | — | — | 0,23 | — |

Rest cobalt including incidental impurities

TABLE 2

| Melt No | Yield strength N/mm$^2$ | Elongation (A$_5$) % | Breakthrough potential[1] mV$_h$ |
|---|---|---|---|
| A | 635 | 9,0 | +760 |
| B | — | — | +1000 |
| 1 | 680 | 4,6 | — |
| 2 | 620 | 4,5 | +850 |
| 3 | 600 | 6,6 | +930 |
| 4 | 560 | 5,4 | +1000 |
| 5 | 550 | 6,4 | +1050 |
| 6 | 560 | 9,0 | +1000 |
| 7 | 570 | 9,2 | +930 |
| 8 | 615 | 3,5 | +980 |
| 9 | 520 | 10,5 | +1040 |
| 10 | 625 | 8,1 | +830 |
| 11 | 655 | 13,1 | — |
| 12 | 630 | 9,1 | — |
| 13 | 655 | 13,3 | +790 |
| 14 | 535 | 12,5 | +980 |
| 15 | 510 | 13,3 | +910 |
| 16 | 570 | 13,6 | +980 |
| 17 | 670 | 4,7 | +830 |
| 18 | 665 | 8,0 | +840 |

A = normal Co—Cr-alloy
B = normal Au—Pt—Pd-alloy
[1] measured according to the Fusayama test method at 37° C. in air in artificial saliva

I claim:

1. Removable dental appliances consisting of a cobalt-chromium cast alloy consisting essentially of (in % by weight):

0,1 to 1,0% carbon 0,05 to 0,5% nitrogen 0,5 to 3,0% silicon 0,3 to 10,0% manganese 20 to 35% chromium 2 to 10% molybdenum 5 to 40% iron at least 20% cobalt as residue including incidental impurities.

2. Removable dental appliances according to claim 1, wherein the content of the sum of carbon and nitrogen in the alloy does not exceed 1%.

3. Removable dental appliances according to claim 1, wherein the alloy consists of 0,1 to 0,5% carbon 0,05 to 0,5% nitrogen 0,9 to 2% silicon 1 to 6% manganese 26 to 31% chromium 2 to 6% molybdenum 20 to 35% iron at least 20% cobalt as residue including incidental impurities.

4. Removable dental appliances according to claim 3, wherein the content of the sum of carbon and nitrogen in the alloy does not exceed 1%.

5. Removable dental appliances according to claim 1 wherein the alloy additionally contains up to 0,5% of at least one of aluminum, boron, columbium and titanium.

6. Removable dental appliances according to claim 5 wherein the alloy additionally contains at least one member of the group consisting of aluminum, boron, columbium and titanium in amounts of 0.01 to 0.2% each.

7. Removable dental appliances according to claim 1 wherein the alloy contains higher amounts of the other alloying elements within the given ranges when iron is added in the amount of 25 to 40%.

* * * * *